United States Patent [19]

Brown

[11] 4,096,467
[45] Jun. 20, 1978

[54] ULTRASONIC IMAGE CONVERSION

[75] Inventor: Patrick Harold Brown, Hillingdon, England

[73] Assignee: E M I Limited, Hayes, England

[21] Appl. No.: 750,980

[22] Filed: Dec. 15, 1976

[30] Foreign Application Priority Data

Dec. 17, 1975 United Kingdom ............... 51724/75

[51] Int. Cl.² .................. G01S 9/66; H01J 31/495
[52] U.S. Cl. ................................. 340/5 MP
[58] Field of Search ........................ 340/5 MP, 5 H

[56] References Cited

U.S. PATENT DOCUMENTS 3,803,606  4/1974  Labail et al. ............... 340/5 H X
3,899,767  8/1975  Jones ........................ 340/5 MP X Primary Examiner—Richard A. Farley
Attorney, Agent, or Firm—Fleit & Jacobson

[57] ABSTRACT

Ultrasonic imaging techniques are subject to interference from whiteout, a component at insonification frequency in the image signal. A technique for separating the image signal from whiteout by mixing the received ultrasonic radiation with another frequency is described. In one form using an electron beam to scan a transducer mosaic the beam is modulated and mixing occurs between the transducer and a signal plate. A filter connected to the signal plate selects a mixing product containing the image signal and rejects the insonification and beam frequencies.

12 Claims, 2 Drawing Figures

ULTRASONIC IMAGE CONVERSION

This invention relates to an ultrasonic image converter tube arrangement.

In an ultrasonic image converter tube arrangement ultrasonic radiation incident on a sensor plate such as a piezo-electric material, e.g. quartz, adjacent a conductive signal plate electrode produces a pattern of voltages representing the amplitude and phase of the mechanical vibrations induced in the plate by the radiation.

An electron beam produced from a cathode in the tube is caused to scan the plate and the beam is incident on a capacitor of which one electrode is formed by the signal plate electrode to cause a current to flow in a load resistor (or amplifier input) connected to the signal plate. The signal current in the load resistor depends on the voltage produced in the sensor plate at the point of incidence of the electron beam which voltage is effectively generated in parallel with the capacitor and is capacitively coupled to the signal plate. The beam effectively holds the sensor surface at the anode potential of the tube.

In addition to this desired current in the load resistor (or amplifier input) there is an unwanted current called "whiteout". This occurs because there is a stray capacitive coupling from all the cathode-facing sensor plate surface to the other tube electrodes which effectively provides a capacitive path, in parallel with the electron beam, through which all the rest of the sensor plate is coupled to the load resistor. A current is caused to flow in this path which is the result of a vector summation of the voltages across the rest of the sensor plate. This current, the whiteout current, degrades the picture by introducing interference fringe patterns and can vary rapidly with the image content.

Electronic cancellation techniques, based on sensing the vector summation of the sensor plate voltage, are only satisfactory with constant image frequency or image line phase which produces a steady whiteout current.

It is an object of the invention to provide an improved ultrasonic image converter.

According to the invention there is provided an ultrasonic image converter tube arrangement including a pick-up tube having, in an envelope, anode and cathode electrodes, an electron beam source and a scannable surface of a sensor plate with a capacitively coupled signal plate having an output terminal connected thereto, means to scan a beam from said source over said scannable surface, means to modulate the current in said scanned beam and, connected to said terminal, means selectively responsive to a frequency component resultant from the mixing of the beam current modulation and the signals representing an image in ultrasonic radiation scanned off the sensor plate which image, in operation of the arrangement, is incident on said plate in ultrasonic radiation, the selectively responsive means rejecting components at the frequency of said ultrasonic radiation.

The means connected to the output terminal may be a low noise "head" amplifier of bandwidth limited to be responsive to the sum or difference of the modulating and tuned frequencies and reject the "whiteout" signal produced at the frequency of the incident radiation. The arrangement may be immersible. The sensor plate may be tuned.

According to the invention there is also provided a method of detecting variations of ultrasonic radiation representing an image in ultrasonic radiation including providing a source of another frequency of a value distinct from the ultrasonic radiation frequency value, applying the another frequency and the ultrasonic frequency to a non-linear means to produce mixing products including at least one modulated by said variations filtering a single mixing product modulated by said variations from other mixing products, including any at said ultrasonic frequency, whereby said variations are obtained as a time-based signal substantially without any component at the ultrasonic frequency.

The another frequency may be an electrical frequency and the ultrasonic frequency may be applied to an ultrasonic to electrical transducer to provide an output for application to the non-linear means with the electrical another frequency.

Embodiments of the invention will be described with reference to the accompanying drawings of which:

Figure 1:
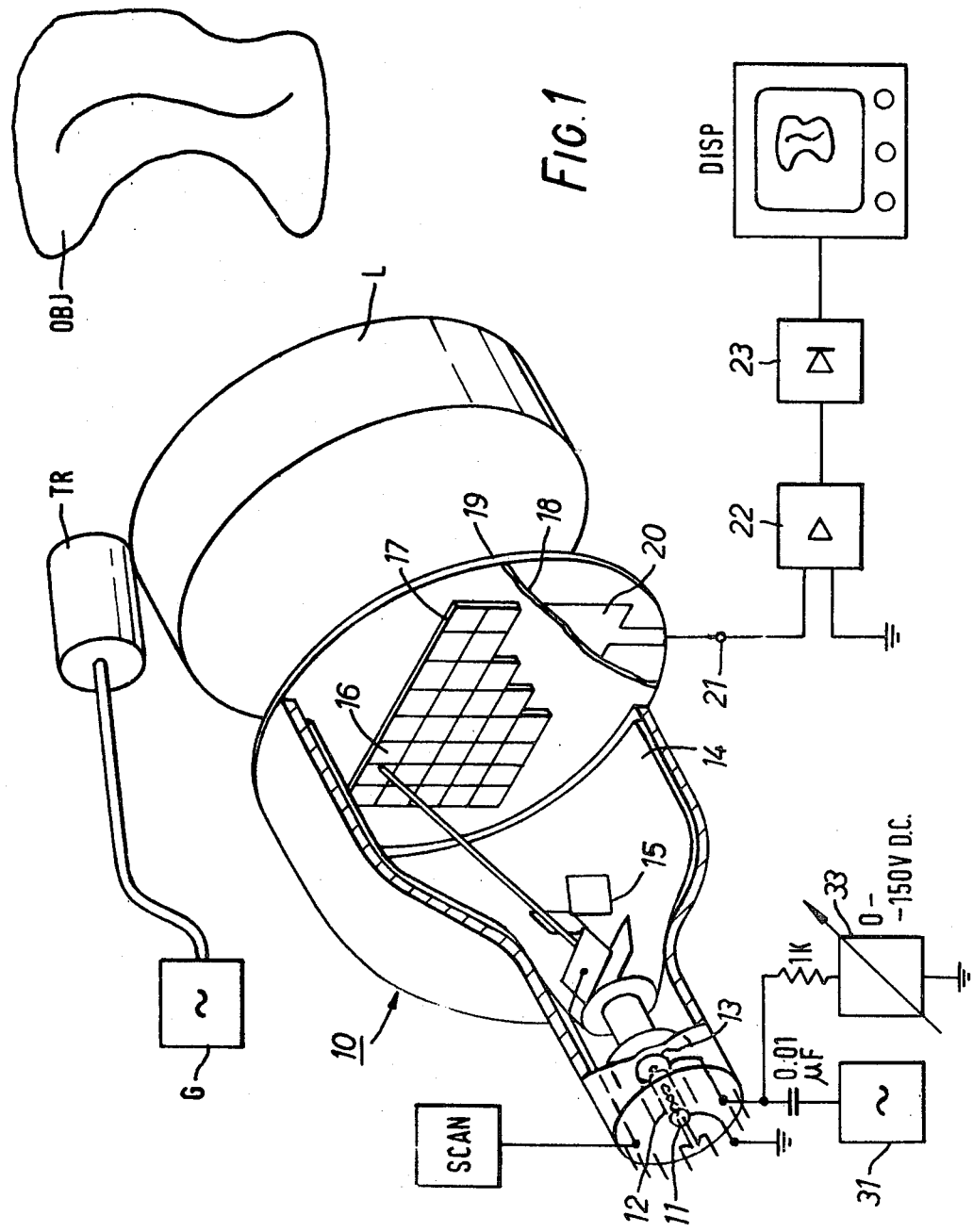
FIG. 1 is a schematic diagram of the arrangement, including the tube.

FIG. 1 shows an ultrasonic image converter tube indicated generally at 10 and its relevent component parts and associated circuitry. The tube 10 has in an envelope a filament 11 heatable to cause electrons to be emitted from a cathode 12 in an electron gun assembly. A grid 13 is positioned so that the intensity of the electron stream from the gun assembly can be controlled.

A wall anode and associated electrodes are arranged for energisation to produce an electron beam. Electrostatically effective beam deflection plates 15 are provided to permit deflection of the electron beam in scanning raster over a surface 16 of a piezo-electric sensor plate 17 exposed inside the envelope. A sheet 18 of a synthetic rubber material such as VITON (Registered Trade Mark) closes the envelope to provide an evacuated space inside the tube 10. The sheet 18 and plate 17 are supported on a plastics face-plate 19 of, e.g. an epoxy resin. An acoustic lens L is placed in front of the tube. Between the sheet 18 and face-plate 19 is an electrode, a signal plate, of a metallised layer 20 provided with a terminal 21. The general form of such tubes is known and will not be described further unless relevant.

In operation of known ultrasonic image tube arrangements the terminal 21 is connected to an amplifier 22 and demodulator 23 and then to a suitable display DISP. However as described above the display obtained when the tube 10 receives ultrasonic radiation reflected from an object OBJ insonified at a selected frequency by ultrasonic energy from generator G radiated by transducer TR is subject to interference from "whiteout". Transducer TR is preferably a ring of transducers around lens L.

To overcome this the beam current of the tube 10 is modulated at a selected frequency and the amplifier 22 is designed to be responsive to a frequency component resulting from the mixing of the modulation frequency and the ultrasonic frequency incident on the face-plate 19. This mixing produces at least one frequency component sufficiently distinct from the "whiteout" component to be separable therefrom by a suitable filter. The modulation frequency must clearly be different from the ultrasonic frequency and preferably not an integral multiple of it.

In a particular example of the invention for use in an underwater environment grid 13 of tube 10 is controlled by an oscillator 31 coupled thereto by capacitor 32. A d.c. bias adjustable between 0 and −150V is also applied to grid 13 by source 33. The cathode 12 is earthed. The oscillator has a frequency of 3MHz and a sine or rectangular or other wave form of some 60v double-amplitude peak. The anode voltage is some 500–1000v.

The d.c. bias and oscillation wave form simultaneously applied to the grid can be adjusted to modulate the beam current to a desired wave form. The modulation of the beam current is effective as mentioned above and specifically described below to reduce white out. Clearly other techniques for beam current modulation can be used.

A particularly effective manner of controlling the grid to modulate the beam is to use a square wave form, i.e. of unity mark/space ratio, oscillation from e.g. oscillator 31 and a d.c. bias. In this way the electron beam current wave form remains stable even if the bias and/or oscillation amplitude change provided cut-off potential is exceeded. In distinction a sine wave would vary the beam current wave form as change in bias and/or amplitude would alter the duration of the sine wave above tube cut off potential.

Furthermore the square wave form for the electron beam current has the maximum possible energy at the fundamental frequency. As a result the signal mixing process will be the most efficient in producing sum and difference frequencies and thereby using the bandpass signal amplifier tuned to such a sum or difference frequency, and thereby maximum output from the image converter tube.

The sensor plate 17 is a group of square quartz tesserae cut to be half-wave resonant at 2MHz, the insonification frequency.

The insonification frequency, from G, is 2MHz and the tube face plate is in contact with the water in which a typical object OBJ or target area is immersed. The 2MHz insonification frequency produces an image in the quartz tesserae at this frequency in the form of voltages. The beam from the cathode 12 modulated at 3MHz is scanned over the sensor plate surface 16 at a rate of 12.5 interlaced frames of a 201 line picture per second.

The relation between image converter output signal current, at terminal 21, and scanning electron beam current is non-linear so mixing occurs at each point of impact of the electron beam on surface 16 while the surface potential is "stabilised" in known manner.

The resultant frequency components capacitively coupled to the signal plate electrode 20 include one centered on 1MHz, i.e. 3MHz − 2MHz, as well as a whiteout component at the insonification frequency (2MHz) and another mixing component centered on 5MHz (3MHz + 2MHz). The whiteout component does not enter the mixing process. The amplifier 22 connected to terminal 21 of electrode 20 includes a filter centered on 1MHz with a pass-band of ±¼ MHz. A suitable amplifier is described below. With this pass-band all frequencies but the desired component of the frequency mixing process can be rejected and only the wanted signal amplified and demodulated, using e.g. known equipment. The 5MHz component may be used instead.

Figure 2:
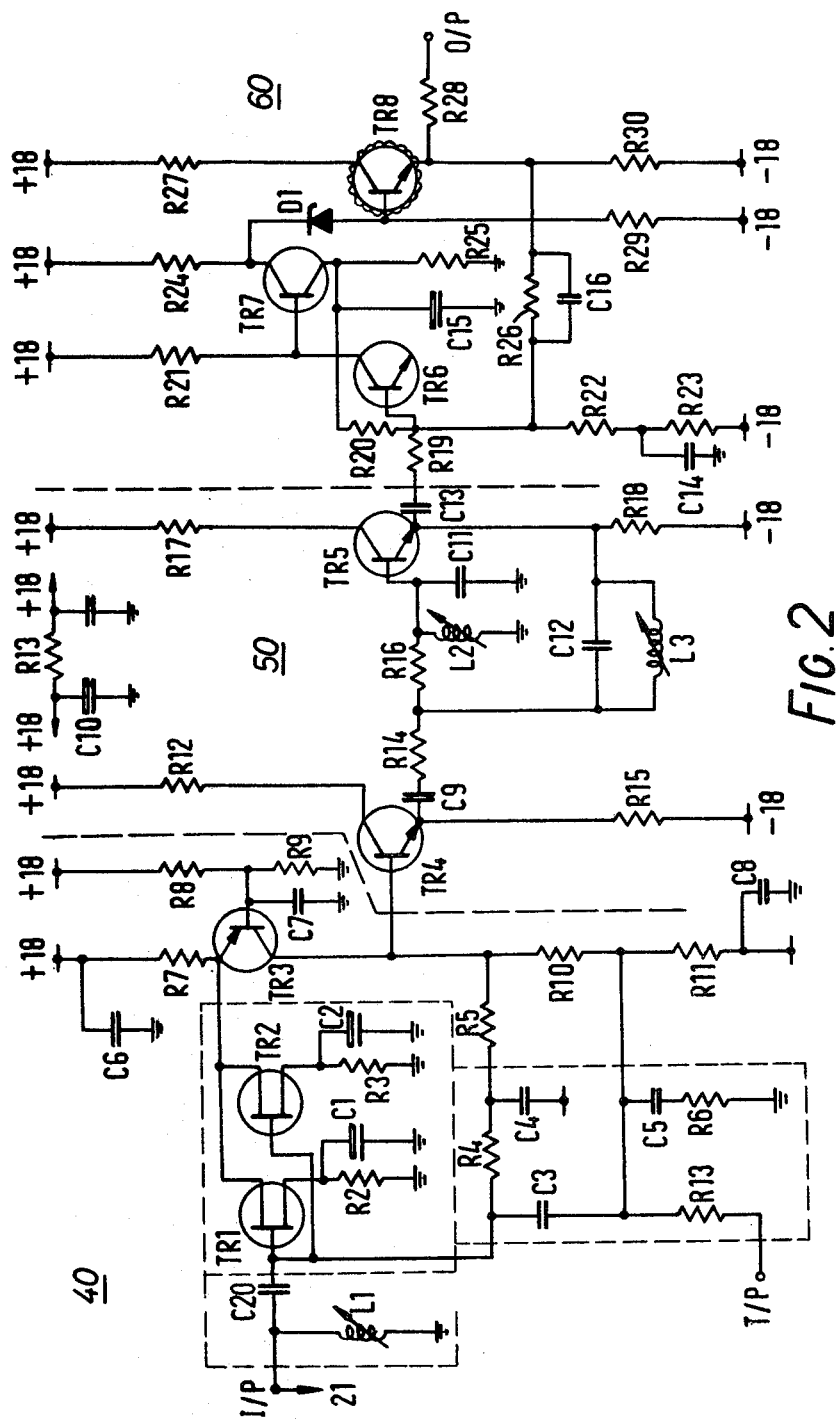
FIG. 2 shows a circuit diagram of an amplifier suitable for use in the arrangement of FIG. 1.

The amplifier 22 must be a low-noise narrow bandwidth device. One suitable form is shown in FIG. 2. The amplifier has three main sections, a tuned low-noise input stage, 40, a band pass stage 50 and an output stage 60.

To achieve a low-noise high-sensitivity input stage parallel-connected field effect transistors are used to provide capacitive matching to the tube. To further reduce the noise the input to the amplifier is arranged as a parallel resonant L stage rather than the series form used hitherto. In this way the pick-up tube capacitance, Cp, and the external capacitance, Ca, of the amplifier input appear in parallel with inductor $L_1$ of FIG. 2. A smaller inductor may be used and the shunt inductor path attenuates low-frequency components. The parallel form also improves the noise performance of the stage. In a series tuned stage the transistor noise signal increases with frequency on applying feed-back to produce a flat frequency response. However a parallel tuned stage produces both a peak in the signal response at the desired frequency and a dip in the transistor noise signal at the same frequency. To benefit from this the equivalent noise from the coil must be less than from the transistor. Coils having a suitable Q to achieve this are not difficult to construct at the frequencies being considered, a suitable Q is between 100 and 200 for two or three E8000 type f.e.t's in parallel operated at 1MHz ± ¼MHz. Feed-back is applied as shown in FIG. 2· to produce a low-pass response as part of a band pass filter formed with part 50 of the amplifier. Here the forward and feed-back paths have LC circuits to provide the double-hump response centered on the desired frequency, to which $L_1$ is tuned.

It is important that there is as little phase change as possible in the amplifier to the feed-back point as phase change will shift the dip in the transistor noise away from the centre frequency set by $L_1$. The open loop amplifier has a high, wide-band gain so screening is desirable as indicated in FIG. 2. Output stage 60 provides a drive at 75Ω. The whole amplifier has a gain of 2V/μA.

If required further filtering can be provided in the amplifier or elsewhere in the display chain to reject breakthrough of the whiteout component or the modulation frequency.

An improved display can be obtained by televising the display using a suitable TV e.g. a "laggy" vidicon, to improve signal/noise ratio by integration and a higher scan rate, e.g. the conventional 25 frames/sec, to reduce flicker.

The above described technique of deriving from a pick-up tube the wanted signal and rejecting whiteout and other components by a modulation or mixing process permits the production of steady viewable pictures under conditions of relative movement where conventional cancellation is unsuitable. A range of 10m is possible at 2MHz.

Clearly other techniques such as cathode modulation and electromagnetic scan may be used.

The technique described above is useful for applications of ultrasonic examination other than in a submarine environment e.g. non-destructive testing in which a sample is clamped against the tube face and insonified from behind. In such a case the whiteout problem is much more severe. Instead of clamping the sample there may be a liquid layer to provide acoustic coupling.

Although described in terms of single frequency insonification the insonification may be of multiple, switched or pulsed frequencies or "narrow-band" noise, i.e. within the system bandwidth. Pseudo-random insonification, the amplitude being constant while the frequency shifts within a restricted bandwidth, is particularly suitable for use with the techniques described above. In such variable frequency situations electronic cancellation is ineffective but the techniques described above have proved most satisfactory.

What I claim is:

1. An ultrasonic image converter tube arrangement including a pick-up tube having, in an envelope, anode and cathode electrodes, an electron beam source and a scannable surface of a sensor plate with a capacitively coupled signal plate having an output terminal connected thereto, means to scan a beam from said source over said scannable surface, means to modulate the current in said scanned beam and, connected to said terminal, means selectively responsive to a frequency component resultant from the mixing of the beam current modulation signal and the signals representing an image in ultrasonic radiation scanned off the sensor plate which image, in operation of the arrangement, is incident on said sensor plate in ultrasonic radiation, the selectively responsive means rejecting components at the frequency of said ultrasonic radiation.

2. An arrangement according to claim 1 in which the sensor plate is tuned to the frequency of the ultrasonic radiation.

3. An arrangement according to claim 1 in which the selectively responsive means includes a band-pass filter having a pass band-width to accept amplitude modulation of the resultant frequency component representing the image.

4. An arrangement according to claim 1 in which the selectively responsive means is a low noise amplifier.

5. An arrangement according to claim 4 in which the amplifier includes low-noise input stage or parallel-connected field effect transistors and a parallel resonant tuned circuit.

6. An arrangement according to claim 1 in which the modulation of the beam current is produced by varying a voltage applied to a grid of the converter tube.

7. An arrangement according to claim 6 in which the beam modulation voltage includes a steady component and an alternating component.

8. An arrangement according to claim 7 in which the alternating component is a square wave at the beam modulation frequency to produce a beam current of substantially equal off/on ratio.

9. An arrangement according to claim 1 in which the beam current is modulated to a substantially equal off-/on ratio.

10. An arrangement according to claim 1 in which the modulation frequency is greater than the tuned frequency of the sensor plate and in which the difference mixing component is selected by the selectively responsive means.

11. A method of detecting variations of ultrasonic radiation representing an image in ultrasonic radiation incident upon a two-dimensional sensor including
providing a source of another frequency of a value distinct from the ultrasonic radiation frequency value,
applying the another frequency and the ultrasonic frequency to a non-linear means in the sensor to produce mixing products including at least one modulated by said variations
filtering a single mixing product modulated by said variations from other mixing products, including any at said ultrasonic frequency, whereby said variations are obtained as a time-based signal substantially without any component at the ultrasonic frequency.

12. A method according to claim 11 in which the another frequency is an electrical frequency and the ultrasonic frequency is applied to an ultrasonic to electrical transducer to provide an output for application to the non-linear means with the electrical another frequency.

* * * * *